US00PP27847P3

(12) United States Plant Patent
Bourne

(10) Patent No.: US PP27,847 P3
(45) Date of Patent: Apr. 4, 2017

(54) ***DIANTHUS* PLANT NAMED 'WP15 VAL12'**

(50) Latin Name: *Dianthus×allwoodii*
Varietal Denomination: WP15 VAL12

(71) Applicant: Plant Genetics International Ltd., Hampshire (GB)

(72) Inventor: Carolyn Grace Bourne, Devon (GB)

(73) Assignee: Plant Genetics International Ltd., Hampshire (GB)

( * ) Notice: Subject to any disclaimer, the term of this patent is extended or adjusted under 35 U.S.C. 154(b) by 0 days.

(21) Appl. No.: 14/757,324

(22) Filed: Dec. 16, 2015

(65) Prior Publication Data

US 2016/0183433 P1 Jun. 23, 2016

(30) Foreign Application Priority Data

Dec. 18, 2014 (QZ) ..... PBR 2104/3486

(51) Int. Cl.
*A01H 5/02* (2006.01)

(52) U.S. Cl.
USPC ..... Plt./276

(58) Field of Classification Search
USPC ..... Plt./276, 277, 281, 282
CPC ..... A01H 5/0233
See application file for complete search history.

*Primary Examiner* — Kent L Bell

(74) *Attorney, Agent, or Firm* — Bethany R. Roahrig; Barbara Campbell; Cochran Freund & Young, LLC

(57) ABSTRACT

A new cultivar of *Dianthus* plant named 'WP15 VAL12' that is characterized by a compact mounding habit, semi-double vibrant bright pink flowers, serrated petal edges, blooming from May through October, with a strong sweet fragrance, glaucous blue-green foliage, and which is suitable for use as a flowering plant in pots and containers and for use as a cut flower and in bouquets, is disclosed.

2 Drawing Sheets

Genus and species: *Dianthus×allwoodii.*
Variety denomination: 'WP15 VAL12'.

CROSS REFERENCE TO RELATED APPLICATIONS

This application claims the benefit of priority under 35 U.S.C. 119(f) to the application for European Community Plant Variety Rights which was filed for the instant plant variety on Dec. 18, 2014, File Number 2014/3486.

BACKGROUND OF THE NEW PLANT

The present invention relates to a new and distinct cultivar of hardy *Dianthus*, commonly known as Garden Pink, which is grown for use as a flowering plant for pots and containers and for planting in the garden and landscape. The new cultivar is known botanically as *Dianthus×allwoodii* and will be referred to hereinafter by the cultivar name 'WP15 VAL12'.

'WP15 VAL12' is a complex hybrid plant that is the product of a long term breeding program conducted in a cultivated area of Houndspool, Dawlish, Devon, United Kingdom. 'WP15 VAL12' was selected in 2012 for its semi-double vibrant bright pink flowers, serrated petal edges, strong sweet fragrance and glaucous blue-green foliage.

'WP15 VAL12' arose and was selected as a seedling which resulted from the open pollination of an existing selection of *Dianthus* from the inventor's breeding program, namely *Dianthus* code name 'VAL 06.27' (unpatented and unreleased) as the female parent plant, by an unknown selection from the breeding program as the male parent plant. The male parent was growing within the inventor's stock of breeding lines.

Asexual reproduction of 'WP15 VAL12' was first accomplished in 2012 in a cultivated area of Houndspool, United Kingdom using the propagation method of shoot cuttings. The inventor has determined that 'WP15 VAL12' is stable and reproduces true to type in successive generations of asexual propagation.

SUMMARY

The following traits have been repeatedly observed and represent the characteristics of the new *Dianthus* cultivar 'WP15 VAL12'. 'WP15 VAL12' has not been tested under all possible conditions and phenotypic differences may be observed with variations in environmental, climatic and cultural conditions, however, without any variance in genotype.

1. 'WP15 VAL12' exhibits a compact mounding habit.
2. 'WP15 VAL12' bears semi-double vibrant bright pink flowers.
3. The margins of the petals of 'WP15 VAL12' are prominently serrated.
4. 'WP15 VAL12' blooms from May through October.
5. The flowers of 'WP15 VAL12' exhibit strong sweet fragrance.
6. 'WP15 VAL12' exhibits glaucous blue-green foliage.
7. At maturity, the height of the foliage mound of 'WP15 VAL12' is 35 cm, and the width is 30 cm to 35 cm.
8. 'WP15 VAL12' is perennial and is hardy at least to minus 15° Centigrade.

9. 'WP15 VAL12' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP15 VAL12' showing colors as true as it is reasonably possible to obtain in colored reproductions of this type. Colors in the photographs may differ from the color values cited in the detailed botanical description, which accurately describe the actual colors of the new variety 'WP15 VAL12'.

Figure 1:
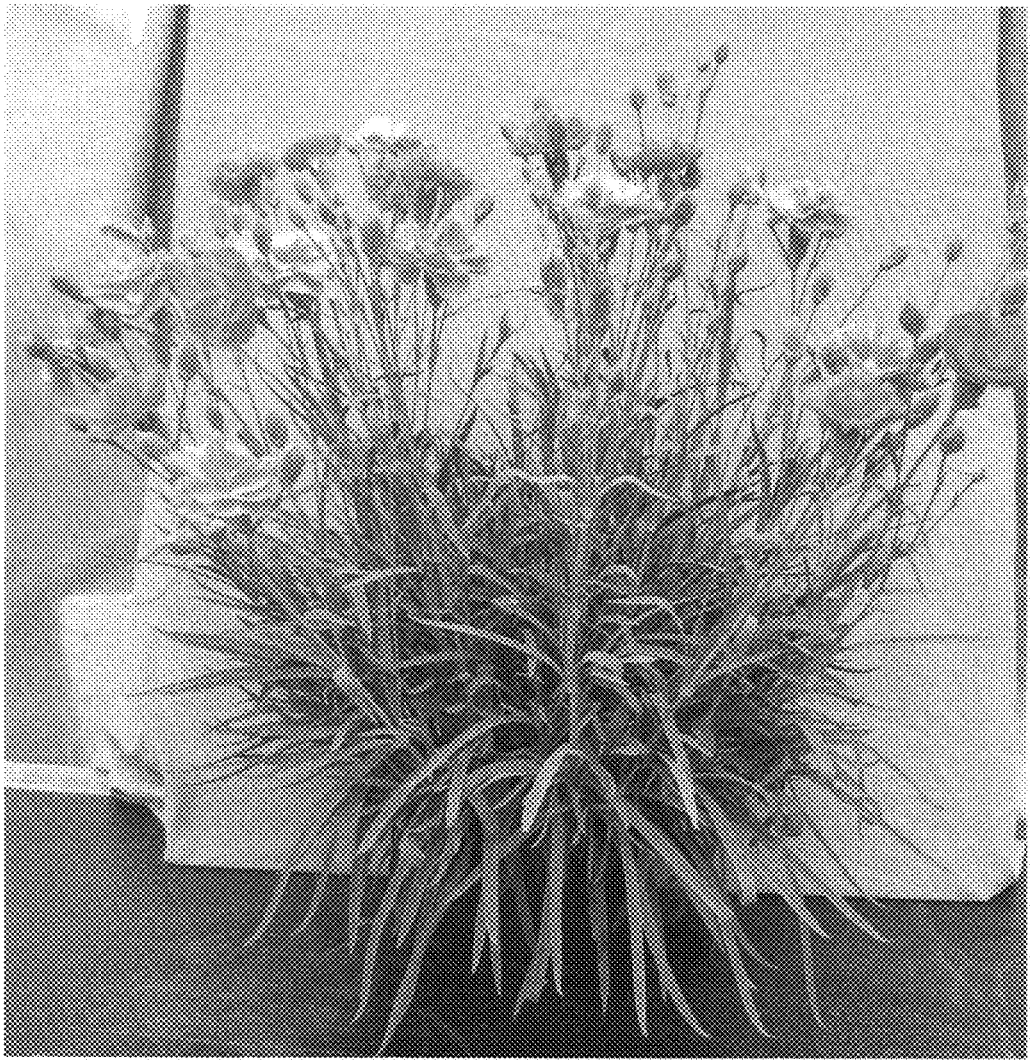
FIG. 1 depicts an entire flowering plant of 'WP15 VAL12'.
Figure 2:
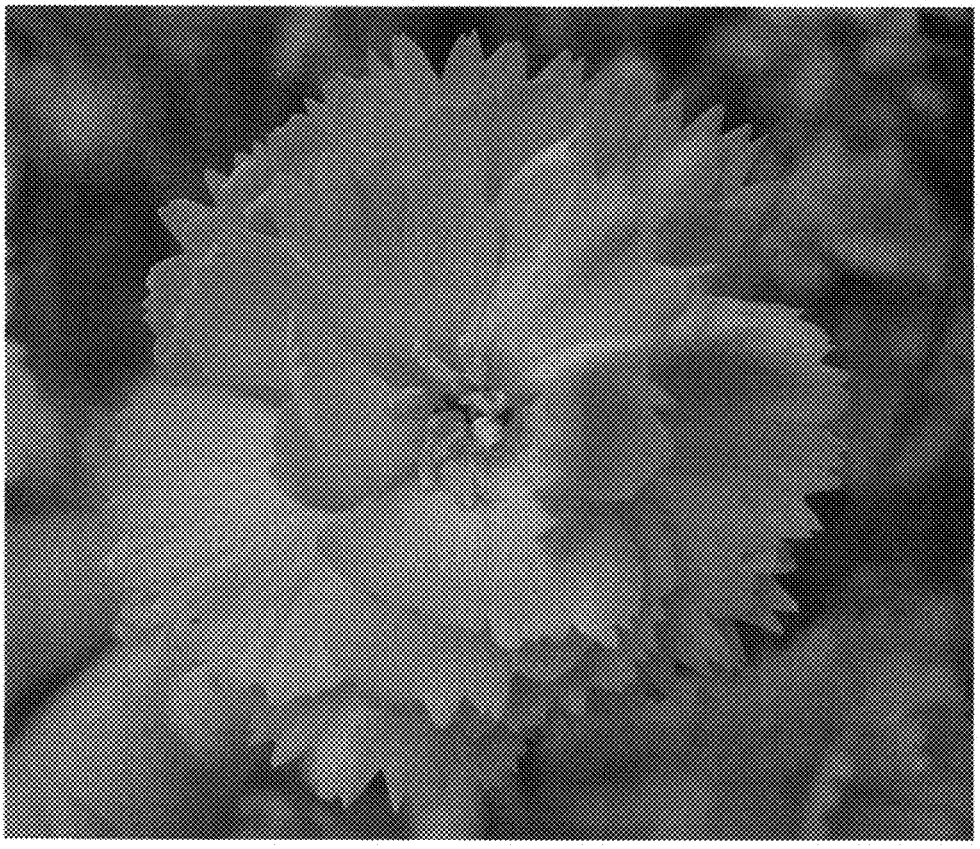
FIG. 2 depicts a close-up view of the flower of 'WP15 VAL12'.

Photographs were taken in June 2015 in Houndspool, Dawlish, Devon, United Kingdom of nine month old plants which have been grown indoor in a 3-liter containers. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP15 VAL12'. Data was collected from plants grown in 3-liter containers under an unheated glasshouse in Houndspool, United Kingdom. The color determinations are in accordance with the 2001 edition of The Royal Horticultural Society Colour Chart of The Royal Horticultural Society, London, England, except where general color terms of ordinary dictionary significance are used. No chemicals were used to treat the plants. Growing conditions are typical of the genus *Dianthus*.

Botanical classification: *Dianthus*.
- *Variety*.—'WP15 VAL12'.
- *Species*.—×*allwoodii*.
- *Common names*.—Hybrid *Dianthus*, Garden Pink.
- *Commercial classification*.—Hardy perennial.
- *Use*.—Ornamental plant for pots and containers.

Parentage: 'WP15 VAL12' is a hybrid plant that resulted from the open pollination between of two *Dianthus*× *allwoodii*.
- *Female parent plant*.—'VAL 06.27' experimental *Dianthus* plant (unpatented).
- *Male parent plant*.—Unknown *Dianthus* plant.

Plant description:
- *Bloom period*.—May to October.
- *Plant habit*.—Compact mounding habit.
- *Plant height*.—35 cm in overall height, including flower canopy.
- *Plant width*.—30 cm to 35 cm in width.
- *Plant hardiness*.—Hardy to minus 15° Centigrade.
- *Type*.—Perennial.
- *Root system*.—Fibrous.
- *Propagation*.—Propagation is accomplished using shoot cuttings.
- *Cultural requirements*.—Plant in full sun, well-drained and moderately fertile soil and keep well fertilized and watered.
- *Time required to produce a rooted cutting*.—5 weeks.
- *Temperature recommended for cuttings to produce roots*.—The air temperature needed is a minimum of 15° Centigrade air temperature and base heat of 21° Centigrade.
- *Crop time*.—6 to 9 months is needed to produce a finished 3-litre container size from a well-rooted cutting.

Stem:
- *Shape*.—Cylindrical, solid.
- *Dimensions*.—13 cm in length, 7 mm diameter.
- *Surface*.—Glabrous and glaucous.
- *Color*.—N189B.
- *Branching*.—Numerous shoots from the axils of the lower leaves.
- *Internode length*.—10 mm between nodes (before extension of peduncle).
- *Node dimensions*.—8 mm in diameter and 6 mm in length.

Leaf:
- *Type*.—Evergreen.
- *Dimensions*.—12 cm in length, 6 mm in width.
- *Color* (*adaxial and abaxial surfaces*).—N189B.
- *Shape*.—Linear.
- *Division*.—Simple.
- *Apex*.—Acute.
- *Base*.—Decurrent.
- *Venation*.—Absent on the adaxial surface and only one central vein visible on the abaxial surface.
- *Margins*.—Entire.
- *Attachment*.—Sheathing.
- *Arrangement*.—Opposite and spiraling up stem.
- *Surfaces* (*adaxial and abaxial*).—Glaucous.
- *Fragrance*.—Absent.

Flowers:
- *Inflorescence type*.—Simple cyme.
- *Flower type*.—Semi-double, polypetalous.
- *Number*.—5 to 8 per stem.
- *Dimensions*.—50 mm in diameter; 44 mm in height, including the calyx.
- *Shape*.—Circular.
- *Lastingness*.—10 days at 20° Celsius on the plant; 8 to 10 days off the plant.
- *Fragrance*.—Strong, sweet.
- *Flowering period*.—May to October.

Peduncle:
- *Shape*.—Cylindrical, solid.
- *Dimensions*.—20 cm to 25 cm in length, 2 mm to 3 mm in diameter.
- *Surface*.—Glabrous, waxy.
- *Strength*.—Strong, rigid.
- *Color*.—122A.

Bud:
- *Shape*.—Obovate.
- *Color*.—137A and N138A (upper or apical half); 143C (basal half).
- *Anthocyanin*.—Absent.
- *Dimensions*.—24 mm in length and 10 mm in width (when about to crack color).

Petals:
- *Corolla*.—Mainly flat but upper part of corolla convex, lower part of corolla concave.
- *Petal arrangement*.—Persistent, apopetalous and overlapping.
- *Number of petals*.—20 to 25.

*Dimensions.*—42 mm to 46 mm in length, 25 mm to 27 mm in width.
*Petal shape.*—Obdeltoid.
*Petal surface.*—Glabrous.
*Petal apex.*—Fan shaped, serrated.
*Petal base.*—Strap shaped, tapering towards base.
*Margin.*—Serrate.
*Indentations (depth).*—Up to 3 mm to 4 mm, irregular.
*Texture.*—Soft.
*Petal color (adaxial surface).*—Ground color of blade. Ranges between N57C and N57D and between 67C and 67D. Color of middle of strap: Whiter than N155A. Color of base of strap: 145D.
*Petal color (abaxial surface).*—Ground color of blade: 64D. Color of middle of strap: Whiter than N155A. Color of base of strap: 145D.

Calyx:
*Dimensions.*—24 mm in depth, 11 mm in width.
*Shape.*—Cylindrical.
*Sepal number.*—5, fused to 5 mm below apex.
*Sepal dimensions.*—24 mm in length and 9 mm in width.
*Apex.*—Subacute.
*Base.*—Truncate.
*Color of sepals, outer surface.*—N138A at sepal apex becoming lighter through N138B, N138C to N138D at sepal base.
*Color of sepals, inner surface.*—138B.
*Anthocyanin.*—Absent.
*Splitting.*—Not observed.

Epicalyx:
*Number of bracts.*—1 pair of 2.
*Bract shape.*—Lanceolate, apex acute.
*Bract dimensions.*—10 mm in length and 8 mm in width.
*Bract color.*—N138B, N138C and N138D are all individually present.
*Anthocyanin.*—Absent.
*Number of bracteoles.*—1 pair of 2.
*Bracteoles shape.*—Lanceolate, apex acuminate.
*Bracteoles dimensions.*—11 mm in length and 10 mm in width.
*Bracteoles color.*—N138B, N138C and N138D are all individually present.
*Bracteoles anthocyanin.*—Absent.

Reproductive organs:
*Stamen number.*—10 to 15 true stamens. Up to 5 petaloid stamens have been observed on individual flowers.
*Stamen dimensions.*—25 mm to 30 mm length and 0.5 mm in diameter.
*Color of filaments.*—Whiter than N155A at base with slight pink hue, close to 62D under the anthers.
*Anther number.*—10 to 15.
*Anther dimensions.*—1 mm length and 0.5 mm in diameter.
*Color of anthers.*—Ranges from whiter than N155A when young, to 62D when mature.
*Anther attachment.*—Dorsifixed.
*Pollen.*—Present, color N155A.
*Style number.*—2.
*Style shoulder.*—Absent.
*Color of style.*—Whiter than N155A.
*Style dimensions.*—25 mm in length and 1 mm in width.
*Stigma number.*—One on each style.
*Stigma color.*—whiter than N155A.
*Stigma dimensions.*—Up to 5 mm long along the top of the style, fimbriated zone barely visible.
*Ovary position.*—Superior.
*Ovary dimensions.*—8 mm in length and 5 mm in diameter.
*Ovary shape.*—Spindle.
*Ovary surface and texture.*—Smooth and slightly ribbed.
*Ovary color.*—145A at uppermost surface, becoming paler 145D at lowest surface.

Seed:
*Quantity.*—1 to 10 seeds per pod.
*Shape.*—Flattened ovoid.
*Dimensions.*—3 mm in length, 2 mm in width.
*Color.*—202A.
*Surface.*—Rough.

Diseases and pests: Susceptible to known *Dianthus* pests and disease but no other susceptibilities to pests or disease are known.

COMPARISON WITH PARENTAL LINE AND KNOWN VARIETY

The identity of the male parent is unknown and therefore a comparison is not possible.

'WP15 VAL12' is distinguishable from the female parent as follows. Whereas the flower shape and color of 'VAL 06.27' is similar to 'WP15 VAL12', the vegetative habit of the two varieties is very different. 'VAL 06.27' exhibits moderate vigor as compared to 'WP15 VAL12' and is more grey-green in color than 'WP15 VAL12'. The overall flower stem count of 'VAL 06.27' is lower and the stems are shorter than that of 'WP15 VAL12'. In addition, the flowers of 'VAL 06.27' are more double and are bicolored dark pink with a crimson eye, whereas the flowers of 'WP15 VAL12' are bright pink in color.

The variety of *Dianthus* considered to most closely resemble 'WP15 VAL12' is 'Valda Wyatt' (unpatented). Whereas both 'WP15 VAL12' and 'Valda Wyatt' bear bright pink flowers which are strongly sweetly fragrant, the flowers of 'Valda Wyatt' are double whereas 'WP15 VAL12' bears semi-double flowers and the flower stems bear a lower count of flowers. In addition, a one year old plant of 'Valda Wyatt' achieves a height of 45 cm whereas a same-age plant of 'WP15 VAL12' is 35 cm in height.

I claim:

1. A new and distinct cultivar of *Dianthus* plant named 'WP15 VAL12' as described and illustrated herein.

* * * * *